(12) United States Patent
Allen et al.

(10) Patent No.: US 7,759,044 B2
(45) Date of Patent: *Jul. 20, 2010

(54) LOW ACTIVATION ENERGY DISSOLUTION MODIFICATION AGENTS FOR PHOTORESIST APPLICATIONS

(75) Inventors: Robert David Allen, San Jose, CA (US); Phillip Joe Brock, Sunnyvale, CA (US); Richard Anthony DiPietro, Campbell, CA (US); Ratnam Sooriyakumaran, San Jose, CA (US); Hoa D. Truong, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 5 days.

This patent is subject to a terminal disclaimer.

(21) Appl. No.: 12/019,676

(22) Filed: Jan. 25, 2008

(65) Prior Publication Data

US 2008/0153034 A1   Jun. 26, 2008

Related U.S. Application Data

(62) Division of application No. 11/239,507, filed on Sep. 29, 2005, now Pat. No. 7,358,029.

(51) Int. Cl.
| | |
|---|---|
| *G03C 1/00* | (2006.01) |
| *C07D 305/00* | (2006.01) |
| *C07D 307/02* | (2006.01) |
| *C07D 307/77* | (2006.01) |
| *C07D 307/00* | (2006.01) |
| *C07D 493/00* | (2006.01) |
| *C07D 307/93* | (2006.01) |
| *C07C 69/74* | (2006.01) |
| *C07C 69/00* | (2006.01) |

(52) U.S. Cl. .................... 430/270.1; 549/263; 549/295; 549/297; 549/313; 549/318; 549/330; 549/456; 549/463; 549/475; 560/1; 560/4

(58) Field of Classification Search .............. 430/270.1; 536/4.1, 17.2, 18.2; 549/263, 295, 297, 313, 549/318, 330, 456, 463, 475; 560/1, 4.1, 560/4

See application file for complete search history.

(56) References Cited

U.S. PATENT DOCUMENTS 5,158,855 A    10/1992   Sugiyama et al.

(Continued)

FOREIGN PATENT DOCUMENTS

WO      WO0231595 A2    4/2002

OTHER PUBLICATIONS

Houle et al.; Determination of Coupled Acid Catalysis-Diffusion Processes in a Positive-Tone Chemically Amplified Photoresist; 2000 American Vacuum Society; J. Vac. Sci. Technol. B18(4), Jul./Aug. 2000; pp. 1874-1885.

(Continued)

*Primary Examiner*—Cynthia H Kelly
*Assistant Examiner*—Connie P Johnson
(74) *Attorney, Agent, or Firm*—Schmeiser, Olsen & Watts

(57) ABSTRACT

A dissolution modification agent suitable for use in a photoresist composition including a polymer, a photoacid generator and casting solvent. The dissolution modification agent is insoluble in aqueous alkaline developer and inhibits dissolution of the polymer in the developer until acid is generated by the photoacid generator being exposed to actinic radiation, whereupon the dissolution modifying agent, at a suitable temperature, becomes soluble in the developer and allows the polymer to dissolve in the developer. The DMAs are glucosides, cholates, citrates and adamantanedicarboxylates protected with acid-labile ethoxyethyl, tetrahydrofuranyl, and angelicalactonyl groups.

20 Claims, 5 Drawing Sheets

U.S. PATENT DOCUMENTS

| | | | |
|---|---|---|---|
| 5,310,619 | A | 5/1994 | Crivello et al. |
| 5,362,607 | A | 11/1994 | Crivello et al. |
| 5,476,751 | A | 12/1995 | Steinmann |
| 5,683,856 | A | 11/1997 | Aoai et al. |
| 5,879,857 | A | 3/1999 | Chandross et al. |
| 5,919,597 | A | 7/1999 | Sinta et al. |
| 6,037,097 | A | 3/2000 | Bucchignano et al. |
| 6,043,003 | A | 3/2000 | Bucchignano et al. |
| 6,060,213 | A | 5/2000 | Kodama |
| 6,103,450 | A | 8/2000 | Choi |
| 6,358,666 | B1 | 3/2002 | Seo et al. |
| 6,497,987 | B1 | 12/2002 | Kim et al. |
| 6,517,991 | B1 | 2/2003 | Kodama et al. |
| 6,593,058 | B1 | 7/2003 | Feiring et al. |
| 6,716,565 | B2 | 4/2004 | Kunita et al. |
| 6,818,377 | B2 | 11/2004 | Kodama et al. |
| 6,962,766 | B2 | 11/2005 | Uenishi et al. |
| 7,108,953 | B2 | 9/2006 | Berger et al. |
| 7,129,017 | B2 | 10/2006 | Yamamoto et al. |
| 7,150,961 | B2 | 12/2006 | Jung et al. |
| 7,358,029 | B2 * | 4/2008 | Allen et al. .............. 430/270.1 |
| 2002/0022197 | A1 | 2/2002 | Jung et al. |
| 2003/0171490 | A1 | 9/2003 | Breyta et al. |
| 2004/0005513 | A1 | 1/2004 | Takahashi et al. |
| 2004/0023150 | A1 | 2/2004 | Feiring et al. |
| 2004/0033436 | A1 | 2/2004 | Berger et al. |
| 2004/0126697 | A1 | 7/2004 | Farnham et al. |
| 2004/0152860 | A1 | 8/2004 | Ogata et al. |
| 2004/0180287 | A1 | 9/2004 | Feiring et al. |
| 2004/0229162 | A1 | 11/2004 | Ohsawa et al. |
| 2005/0026073 | A1 | 2/2005 | Sasaki |

OTHER PUBLICATIONS

Hinsberg et al.; Extendibility of Chemically Amplified Resists: Another Brick Wall?; Advances in Resist Technology and Processing XX, Theodore H. Fedynyshyn, Editor, Proceedings of SPIE vol. 5039 (2003); 0277-786X/03; pp. 1-14.

Houle et al.; Effect of Resist Components on Image Spreading During Postexposure Bake of Chemically Amplified Resists; SPIE 3999, 148 (2000); 13 pages.

* cited by examiner

LOW ACTIVATION ENERGY DISSOLUTION MODIFICATION AGENTS FOR PHOTORESIST APPLICATIONS

RELATED APPLICATIONS

This Application is a division of application Ser. No. 11/239,507 filed on Sep. 29, 2005 now U.S. Pat. No. 7,358,029.

FIELD OF THE INVENTION

This invention relates generally to the field of photolithography. More specifically, the invention relates to chemically amplified photoresist system compositions containing dissolution modification agents, methods of using chemically amplified photoresist system compositions containing dissolution modification agents and dissolution modification agents for chemically amplified resist systems.

BACKGROUND OF THE INVENTION

The patterning of radiation sensitive polymeric films with actinic radiation such as ultraviolet light at wavelengths of 436, 365, 257, 248, 193 or 157 nanometers (nm) is the principle means of defining high resolution circuitry found in semiconductor devices. The radiation sensitive films, often referred to as photoresists, generally consist of multi-component formulations that are coated onto a desired substrate. The radiation is exposed patternwise and induces a chemical transformation that renders the solubility of the exposed regions of the films different from that of the unexposed areas when the films are treated with an appropriate developer.

Chemically amplified photoresists are based on a catalytic mechanism that allows a relatively large number of chemical events such as, for example, de-protection reactions in the case of positive photoresists or cross-linking reactions in the case of negative tone photoresists, to be brought about by the application of a relatively low dose of radiation that induces formation of a catalyst, often a strong acid. However, chemically amplified photoresists, particularly in the sub-50 nm regime, experience diminished image resolution or contrast, often referred to as "image blur."

Therefore, there is an ongoing need for new photoresist compositions having improved image resolution capability as well as improved methods of patterning substrates.

SUMMARY OF THE INVENTION

A first aspect of the present invention is a dissolution agent represented by one of the following structures:

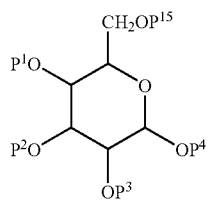

(I)

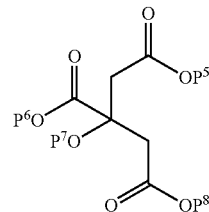

(II)

wherein each $P^1$, $P^2$, $P^3$, $P^4$, $P^5$, $P^6$, $P^7$, $P^8$, and $P^{15}$ is independently selected from the group consisting of a structure V, a structure VI and a structure VII:

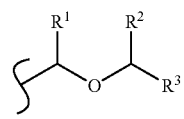

(V)

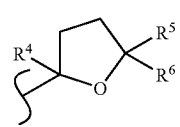

(VI)

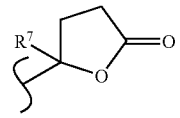

(VII)

wherein each $R^1$, $R^2$, $R^3$, $R^4$, $R^5$, $R^6$ and $R^7$ is independently selected from the group consisting of a hydrogen atom, a hydrocarbyl group having 4 to 12 carbon atoms, a substituted hydrocarbyl group having 4 to 12 carbon atoms, a heterohydrocarbyl group having 4 to 12 carbon atoms, and a substituted heterohydrocarbyl group having 4 to 12 carbon atoms; and wherein any two $R^1$, $R^2$, $R^3$ or any two $R^4$, $R^5$, $R^6$ may be linked to form a three to eight-membered cyclic group.

BRIEF DESCRIPTION OF DRAWINGS

The features of the invention are set forth in the appended claims. The invention itself, however, will be best understood by reference to the following detailed description of an illustrative embodiment when read in conjunction with the accompanying drawings, wherein:

DETAILED DESCRIPTION OF THE INVENTION

Chemically amplified (CA) positive photoresists described by the various embodiments of the present invention are intended to be developed in an aqueous developer and include a polymer that is soluble in an aqueous alkaline solution, a dissolution modification agent (DMA), and a photoacid generator (PAG), all usually dissolved in a casting solvent. The PAG generates acid upon exposure to actinic radiation.

Image blur in such a photoresist system is generally thought to result from two contributing factors: gradient-driven diffusion of acid from exposed into non-exposed regions and reaction propagation. Acid diffusion is thought to depend upon such factors as the type of PAG and acid moiety mobility in the photoresist polymer. Acid mobility in a photoresist layer is dependent on a variety of factors, including the chemical functionality of the polymer and the temperature of the photoresist layer. Reaction propagation is thought to depend upon such factors as the activation energy (enthalpy) and the volatility of reaction products (entropy). Both acid diffusion and acid mobility increase with increasing temperature with resultant increasing image blur.

DMAs according to various embodiments of the present invention are hydrophobic and insoluble in aqueous alkaline developer, thus inhibiting polymer dissolution in the unexposed regions of photoresist layers. In some examples, the polymer itself may be soluble in aqueous alkaline developer, but is inhibited from dissolving in the developer by the strong hydrophobic nature of the DMA. At the same time, DMAs according to various embodiments of the present invention, when activated, become hydrophilic and soluble in aqueous alkaline developer and thus enhance polymer dissolution in the exposed regions of photoresist layers. When activated, the DMA become soluble and hydrophilic and no longer inhibits solution of the polymers in the exposed regions of the photoresist layer. DMAs are activated by the acid released by the PAG at temperatures dependent upon the activation energy of protected acid-labile moieties of the DMAs.

Since it is advantageous to minimize the temperature to which exposed photoresist layers are subjected (to minimize image blur), the various embodiments of the present invention utilize DMAs that are relatively small molecules containing polar and/or base-soluble moieties which are protected by low activation (e.g. low temperature) acid-labile functionalities.

FIGS. 1A through 1G are cross-sectional views of an exemplary photoresist patterning method according to the various embodiments of the present invention.

Figure 1A:
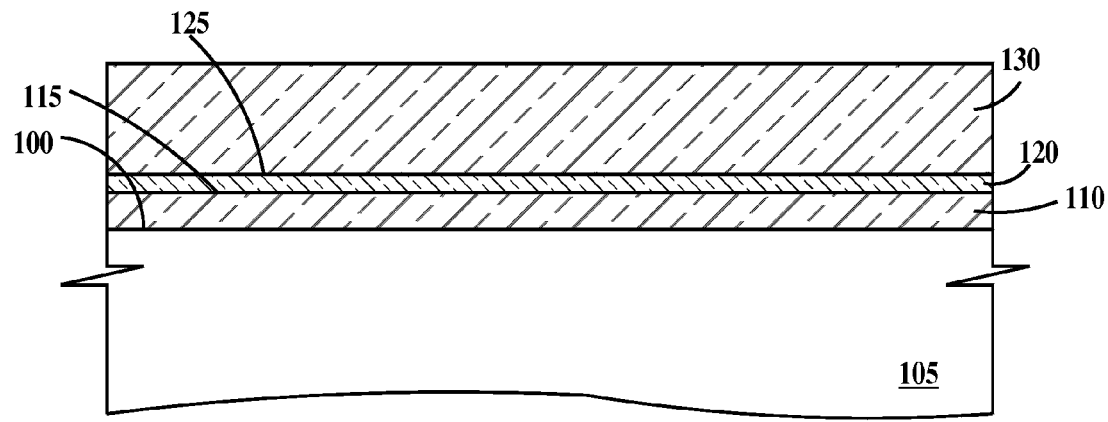
FIGS. 1A through 1G are cross-sectional views of an exemplary photoresist patterning method according to the various embodiments of the present invention.

In FIG. 1A, formed on a top surface 100 of a substrate 105 is an optional insulating layer 110. In one example, substrate 100 is selected from the group consisting of a metal substrate, a ceramic substrate, an organic substrate, a bulk silicon substrate, a silicon-on-insulator substrate and other semiconductor substrates. In one example, layer 110 comprises silicon dioxide, silicon nitride, silicon oxynitride and combinations thereof. Layer 110 may include other insulating materials as is known in the art of integrated circuit manufacture. Alternatively, layer 110 may be replaced by a conductive layer or a semi-conductive layer as is known in the art of integrated circuit manufacture.

Formed on a top surface 115 of layer 110 is an optional anti-reflective coating (ARC). In one example, ARC 115 comprises a diazonaphthoquinone (DNQ)/novolak resist material. ARC 115 may be formed on top surface 105 of substrate 100 if there is no layer 110.

Formed on a top surface 125 of ARC 120 is a photoresist layer 130. Photoresist layer 130 may be formed by spin or spray coating, or doctor blading a layer of a photoresist composition on ARC 120, or on layer 110 if there is no ARC 120 or on substrate 105 if there is no ARC 120 or layer 110. The composition of photoresist layer 130, includes a one or more polymers (at least one not soluble in aqueous alkaline developer), a PAG, a DMA and an optional casting solvent.

In one example, the DMA comprises a material represented by at least one of one of the following (I, II, III, IV) structures:

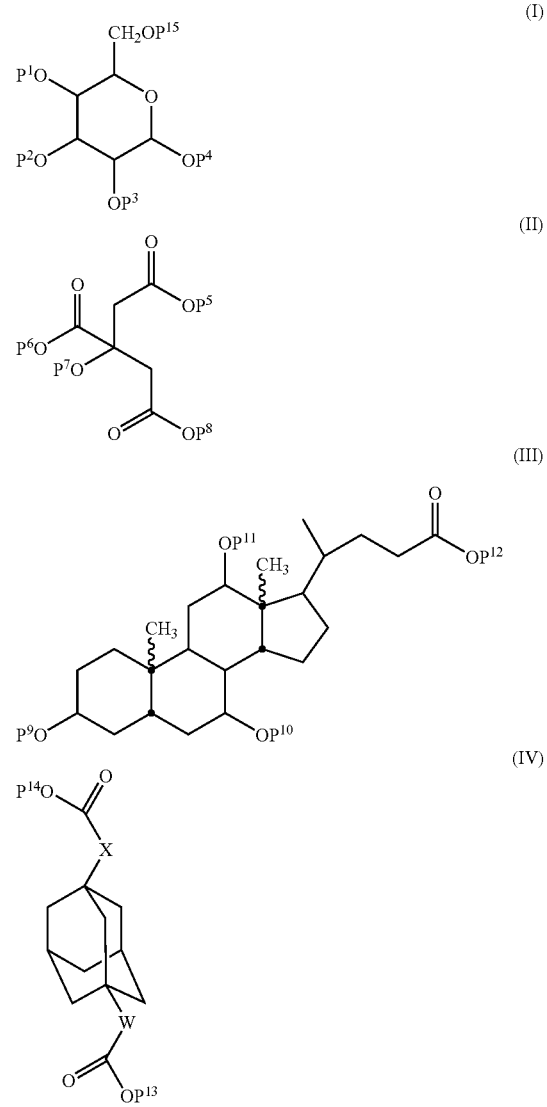

wherein each $R^1$, $R^2$, $R^3$, $R^4$, $R^5$, $R^6$ and $R^7$ is independently selected from the group consisting of a hydrogen atom, a hydrocarbyl group having 4 to 12 carbon atoms, a substituted hydrocarbyl group having 4 to 12 carbon atoms, a heterohydrocarbyl group having 4 to 12 carbon atoms, and a substituted heterohydrocarbyl group having 4 to 12 carbon atoms; and wherein any two $R^1$, $R^2$, $R^3$ or any two $R^4$, $R^5$, $R^6$ may be linked to form a three to eight-membered cyclic group.

wherein W and X are independently selected from the group consisting of an alkylene group having 1 to 12 carbon atoms, and a fluorinated alkylene group having 1 to 12 carbon atoms;

wherein each $P^1$, $P^2$, $P^3$, $P^4$, $P^5$, $P^6$, $P^7$, $P^8$, $P^9$, $P^{10}$, $P^{11}$, $P^{12}$, $P^{13}$, $P^{14}$, and $P^{15}$ is independently selected from the group consisting of a structure V, a structure VI and a structure VII:

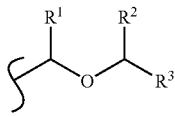

(V)

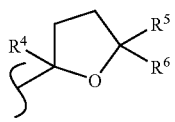

(VI)

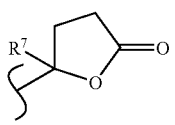

(VII)

wherein each $R^1$, $R^2$, $R^3$, $R^4$, $R^5$, $R^6$ and $R^7$ is independently selected from the group consisting of a hydrogen atom, a hydrocarbyl group having 4 to 12 carbon atoms, a substituted hydrocarbyl group having 4 to 12 carbon atoms, a heterohydrocarbyl group having 4 to 12 carbon atoms, and a substituted heterohydrocarbyl group having 4 to 12 carbon atoms; and wherein any two $R^1$, $R^2$, $R^3$ or any two $R^4$, $R^5$, $R^6$ may be linked to form a three to eight-membered cyclic group.

Structure I is a glucoside, structure II is a citrate, structure III is a cholate and structure IV is an adamantanedicarboxylate. The protecting group of structure V is an ethoxyethyl group, the protecting group of structure VI is a tetrahydrofuranyl group, and the protecting group of structure VII is an angelicalactone.

In a first example, the polymer comprises repeating units of one or more monomers represented by the following structures:

$$M^1\text{-}R^8 \quad (VIII_i)$$

$$M^2\text{-}R^9 \quad (VIII_{ii})$$

$$M^3\text{-}R^{10} \quad (VIII_{iii})$$

where $M^1$, $M^2$ and $M^3$ are independently selected from the group consisting of an alkylene group having 2 to 12 carbon atoms, a substituted alkylene group having 2 to 12 carbon atoms, a heteroalkylene group having 2 to 12 carbon atoms, a substituted heteroalkylene group having 2 to 12 carbon atoms, an alicyclic group having 3 to 15 carbon atoms, and a fluoroalicyclic group having 3 to 15 carbon atoms;

where $R^8$ has a structure $-R^{11}-CR^{12}R^{13}-OH$, in which:

$R^{11}$ is selected from the group consisting of an alkylene group having 2 to 12 carbon atoms, a substituted alkylene group having 2 to 12 carbon atoms, a heteroalkylene group having 2 to 12 carbon atoms, a substituted heteroalkylene group having 2 to 12 carbon atoms, an alicyclic group having 3 to 15 carbon atoms, and a fluoroalicyclic group having 3 to 15 carbon atoms;

$R^{12}$ is selected from the group consisting of a hydrogen atom, an alkyl group having 1 to 24 carbon atoms, a substituted alkyl group having 1 to 22 carbon atoms, and a fluorinated alkyl group having 1 to 24 carbon atoms;

$R^{13}$ is selected from the group consisting of a hydrogen atom, an alkyl group having 1 to 24 carbon atoms, and a fluorinated alkyl group having 1 to 24 carbon atoms; and wherein $R^{12}$ and $R^{13}$ may be linked to form a 3 to 8 carbon atom cyclic ring;

wherein $R^9$ has a structure $-R^{14}-NH-SO_2R^{15}$, in which:

$R^{14}$ is selected from the group consisting of an alkylene group having 2 to 12 carbon atoms, a substituted alkylene group having 2 to 12 carbon atoms, a heteroalkylene group having 2 to 12 carbon atoms, a substituted heteroalkylene group having 2 to 12 carbon atoms, an alicyclic group having 3 to 15 carbon atoms, and a fluoroalicyclic group having 2 to 12 carbon atoms; and $R^{15}$ is selected from the group consisting of a hydrogen atom, an alkyl group having 1 to 24 carbon atoms, a fluorinated alkyl group having 1 to 24 carbon atoms, a substituted alkyl group having 1 to 24 carbon atoms, and a fluorinated alkyl group having 1 to 24 carbon atoms; and wherein $R^{10}$ has a structure $-R^{16}-COOH$, in which:

$R^{16}$ is selected from the group consisting of an alkylene group having 2 to 12 carbon atoms, a substituted alkylene group having 2 to 12 carbon atoms, a heteroalkylene group having 2 to 12 carbon atoms, a substituted heteroalkylene group having 2 to 12 carbon atoms, an alicyclic group having 3 to 15 carbon atoms, and a fluoroalicyclic group having 3 to 15 carbon atoms.

In a second example, the polymer comprises repeating units of one or more monomers represented by the following structures:

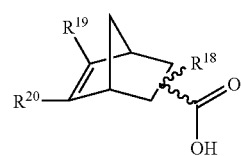

(IX)

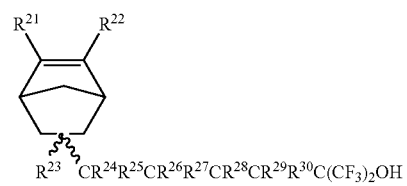

(X)

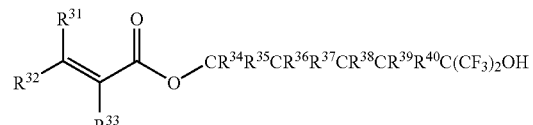

(XI)

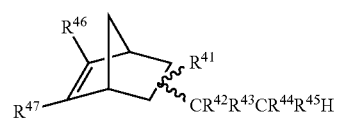

(XII)

wherein each $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$ $R^{42}$, $R^{43}$, $R^{44}$, $R^{45}$, $R^{46}$ and $R^{47}$ ($R^{18}$-$R^{47}$) is independently selected from the group consisting of a hydrogen atom and a hydrocarbyl substituent with a primary, secondary or tertiary carbon attachment point, said hydrocarbyl substituent selected from the group consisting of a linear alkyl or an alkoxy group having 1-6 carbon atoms, a branched alkyl group having 2-12 carbon atoms, an alkoxy group having 2-12 carbon atoms, a cycloalkyl group having 3-17 carbon atoms, a bicycloalkyl group having 3-17 carbon atoms, a cycloalkoxy having 3-17 carbon atoms, a bicycloalkoxy group having 3-17 carbon atoms, a fluorinated linear alkyl group having 2-12 carbon atoms, a fluorinated branched alkyl group having 2-12 carbon atoms, a fluorinated cycloalkyl group having 3-17 carbon atoms, an alkenyl group having 2-12 carbon atoms, a cycloalkenyl group having 2-12 carbon atoms, a dihydropyranyl group, a dihydrofuranyl group, an alkalkenyl group having 2-12 carbon atoms, an alkenylalkyl group having 2-12 carbon atoms, an alkynyl group having 2-12 carbon atoms, an alkalkynyl group having 2-12 carbon atoms, an alkynylalkyl group having 2-12 carbon atoms, a trifluoromethyl group, a trifluoroethyl group, a trifluoropropyl group, and a cyanopropyl group; and wherein any two of $R^{18}$-$R^{20}$, $R^{21}$-$R^{30}$, $R^{31}$-$R^{39}$ and $R^{40}$-$R^{47}$ in the same molecule may be linked to form a 3 to 8 carbon atom cyclic ring.

In a third example, the polymer comprises repeating units of one or more monomers represented by the following structures:

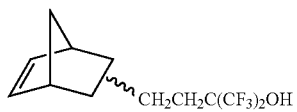
(XIII)

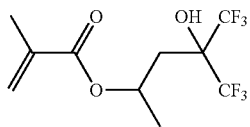
(XIV)

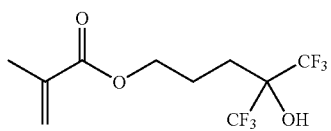
(XV)

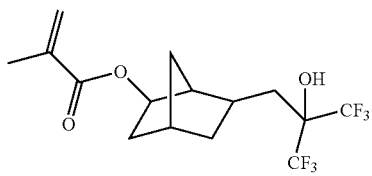
(XVI)

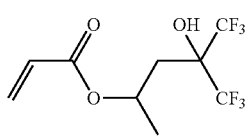
(XVII)

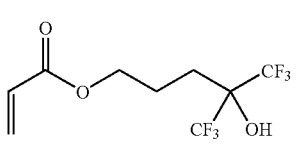
(XVIII)

-continued

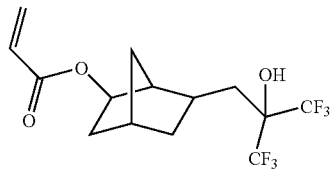
(XIX)

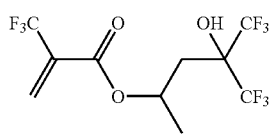
(XX)

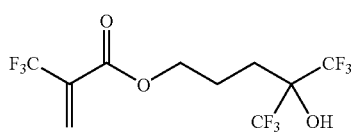
(XXI)

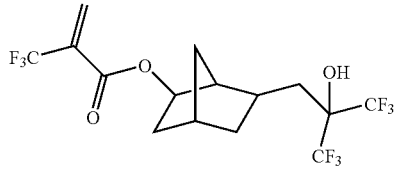
(XXII)

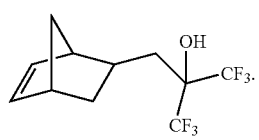
(XXIII)

In a fourth example, the polymer comprises repeating units of one or more monomers represented by the following structures:

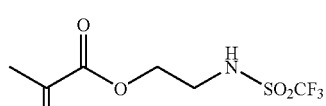
(XXIV)

(XXV)

(XXVI)

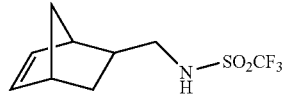
(XXVII)

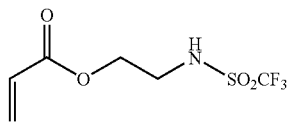
(XXVIII)

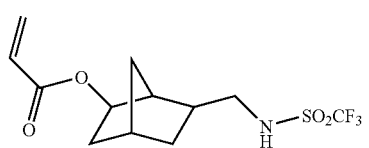

-continued

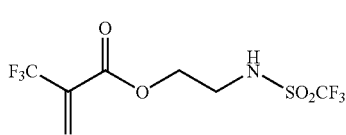
(XXIX)

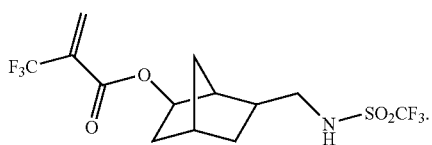
(XXX)

In a fifth example, the polymer comprises repeating units of one or more monomers represented by the following structures:

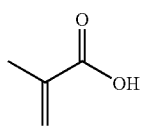
(XXXI)

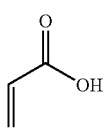
(XXXII)

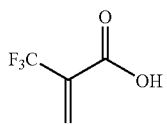
(XXXIII)

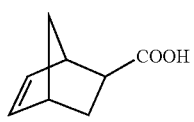
(XXXIV)

In a sixth example, the polymer comprises repeating units of one or more monomers represented by the following structures:

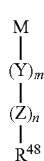
(XXXV)

wherein M is a polymerizable backbone moiety;

wherein each $Y_m$ at each occurrence is independently selected from the group consisting of —C(O)O—, —C(O)—, —OC(O)—, —O—C(O)— and —C(O)—O—;

wherein each $Z_n$ at each occurrence is independently selected from the group consisting of an alkylene group having 1 to 12 carbon atoms, a fluorinated alkylene group having 1 to 12 carbon atoms, a heteroalkylene group having 1 to 12 carbon atoms, an alicyclic group having 3 to 15 carbon atoms, and a fluoroalicyclic group having 3 to 15 carbon atoms;

wherein (a) m and n are both 1, (b) m is 1 and n is 0 or (c) m is 0 and n is 1; and wherein each occurrence of $R^{48}$ is independently selected from the group consisting of a hydrogen atom, a hydroxyl group, a hydroxy substituted alkylene having 1 to 12 carbon atoms, a hydroxy substituted fluoroalkylene having 1 to 12 carbon atoms, a bis-trifluoromethylmethanol group, and an alkylsulfonamide group having 1 to 12 carbon atoms.

In a first example the PAG comprises a sulfonium salt.

In a second example, the PAG is selected from is selected from the group consisting of sulfonium salts, triphenylsulfonium perfluoromethanesulfonate (triphenylsulfonium triflate), triphenylsulfonium perfluorobutanesulfonate, triphenylsulfonium perfluoropentanesulfonate, triphenylsulfonium perfluorooctanesulfonate, triphenylsulfonium hexafluoroantimonate, triphenylsulfonium hexafluoroarsenate, triphenylsulfonium hexafluorophosphate, triphenylsulfonium bromide, triphenylsulfonium chloride, triphenylsulfonium iodide, 2,4,6-trimethylphenyldiphenylsulfonium perfluorobutanesulfonate, 2,4,6-trimethylphenyldiphenylsulfonium benzenesulfonate, tris(t-butylphenyl)sulfonium salts, diphenylethylsulfonium chloride, phenacyldimethylsulfonium chloride, halonium salts, diphenyliodonium perfluoromethanesulfonate (diphenyl)odonium triflate), diphenyliodonium perfluorobutanesulfonate, diphenyliodonium perfluoropentanesulfonate, diphenyliodonium salts, diphenyliodonium hexafluoroantimonate, diphenyliodonium hexafluoroarsenate, bis-(t-butylphenyl)iodonium triflate, bis-(t-butylphenyl)-iodonium camphorsulfonate, a, α'-bis-sulfonyl-diazomethanes, bis(p-toluenesulfonyl)diazomethane, methylsulfonyl p-toluenesulfonyldiazomethane, 1-cyclohexylsulfonyl-1-(1,1 dimethylethylsulfonyl) diazomethane, bis(cyclohexylsulfonyl)diazomethane, trifluoromethanesulfonate esters of imides and hydroxyimides, (trifluoromethylsulfonyloxy)-bicyclo [2.2.1]hept-5-ene-2,3-dicarboximide (MDT), nitrobenzyl sulfonate esters, 2-nitrobenzyl p-toluenesulfonate, 2,6-dinitrobenzyl p-toluenesulfonate, 2,4-dinitrobenzyl p-trifluoromethylbenzenesulfonate; sulfonyloxynaphthalimides, N-camphorsulfonyloxynaphthalimide and N-pentafluorophenylsulfonyloxynaphthalimide; pyrogallol derivatives (e.g., trimesylate of pyrogallol), naphthoquinone-4-diazides, alkyl disulfones, s-triazine derivatives; sulfonic acid generators, N-hydroxynaphthalimide dodecane sulfonate (DDSN) and benzoin tosylate.

In one example the casting solvent is selected from the group consisting of cyclohexanone, ethyl lactate, propylene glycol methyl ether acetate, gamma-butyrolactone and combinations thereof.

In one example, the photoresist composition comprises about 8% by weight to about 15% by weight of polymer, about 1% by weight to about 3% by weight of PAG and about 10% by weight to about 15% by weight of DMA.

Preferably, before photoresist layer 130 is exposed to actinic radiation, the photoresist layer is heated to drive out casting solvent (pre-exposure baked or pre-baked) to a temperature of about 90° C. to about 110° C. for about 1 minute. In one example, photoresist layer 130 has a thickness of about 0.02 micron to about 5.0 microns, preferably about 0.05 micron to about 2.5 microns and most preferably about 0.10 micron to about 1.0 microns.

Figure 1B:
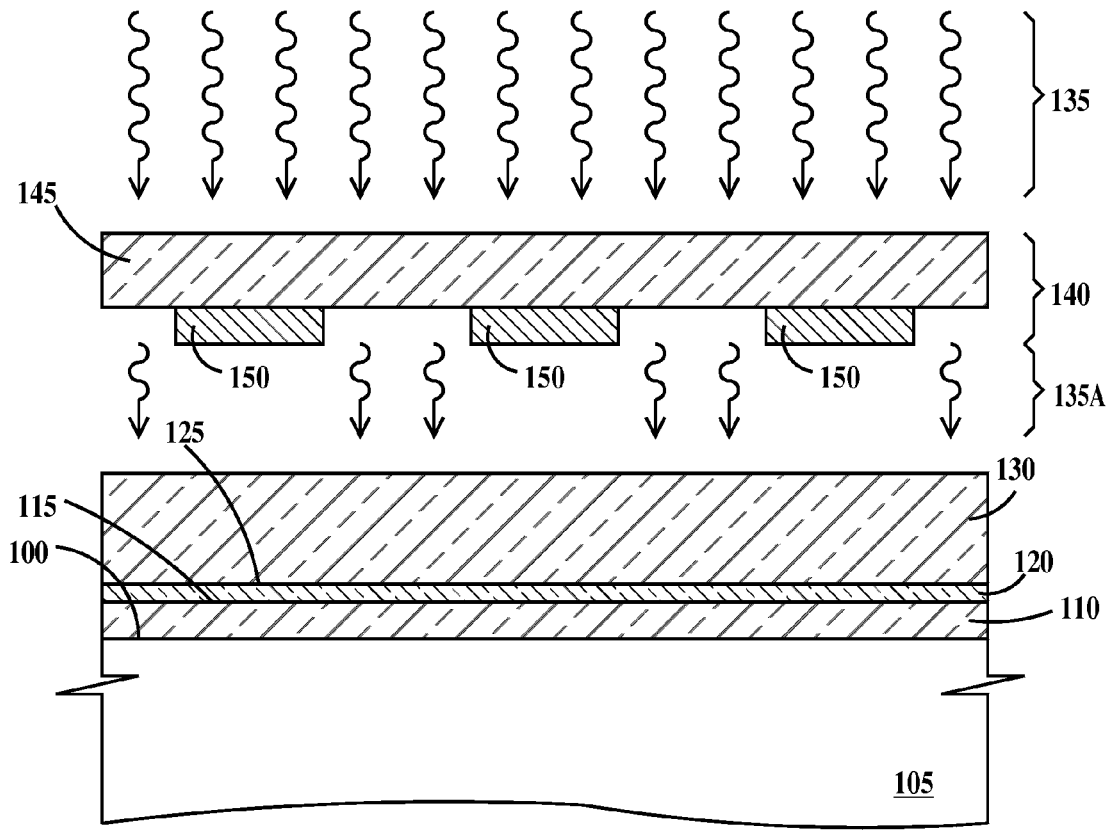

In FIG. 1B, photoresist layer 130 is exposed to actinic radiation 135 through an exemplary mask 140. Mask 140 includes a transparent substrate 145 and opaque islands 150. Other types of masks such as phase contrast masks may be used as well. Portions 135A of actinic radiation 135 pass through transparent region 145 and strike photoresist layer 130 while other portions of the actinic radiation are blocked by opaque islands 150. In regions of photoresist layer 130 struck by portions 135A of actinic radiation 135, the PAG in those regions generates an acid. Actinic radiation 135 may be ultraviolet, electron beam or x-ray. Ultraviolet radiation is preferred, particularly deep ultraviolet radiation having a wavelength of less than about 250 nm and preferably about 193 nm or less.

Figure 1C:
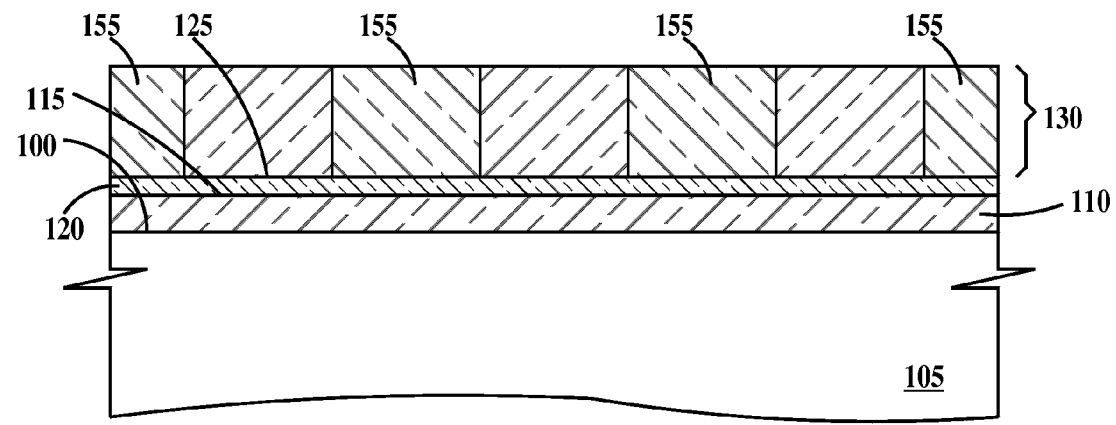

In FIG. 1C, upon heating photoresist layer 130 (see FIG. 1B) to a temperature of between about 26° C. and about 100° C., preferably below 80° C., more preferably below 50° C. and most preferably to just above room temperature (about 26° C.), the acid generated by the PAG causes cleavage of the acid-labile groups of the DMAs. This causes formation of latent images 155 in photoresist layer 130. However, the acid-labile groups of the DMAs in non-exposed regions of photoresist layer 130 are not activated since no acid was generated by the PAG.

Figure 1D:
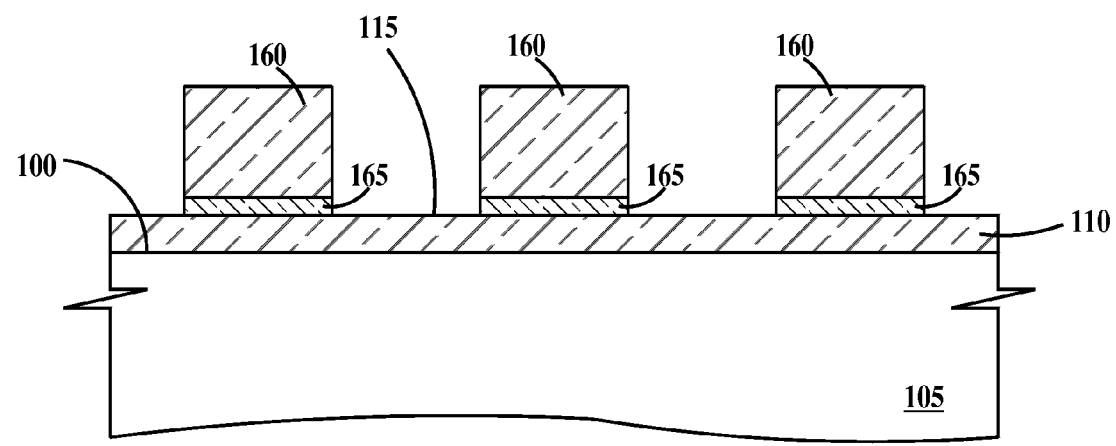

In FIG. 1D, photoresist layer 130 (see FIG. 1C) is developed in an aqueous alkaline solution of a strong base such as tetramethylammonium hydroxide or choline to form photoresist islands 160. Any ARC 120 (see FIG. 1C) not protected by photoresist islands 160 is also removed forming ARC islands 165 exposing top surface 115 of layer 110.

Figure 1E:
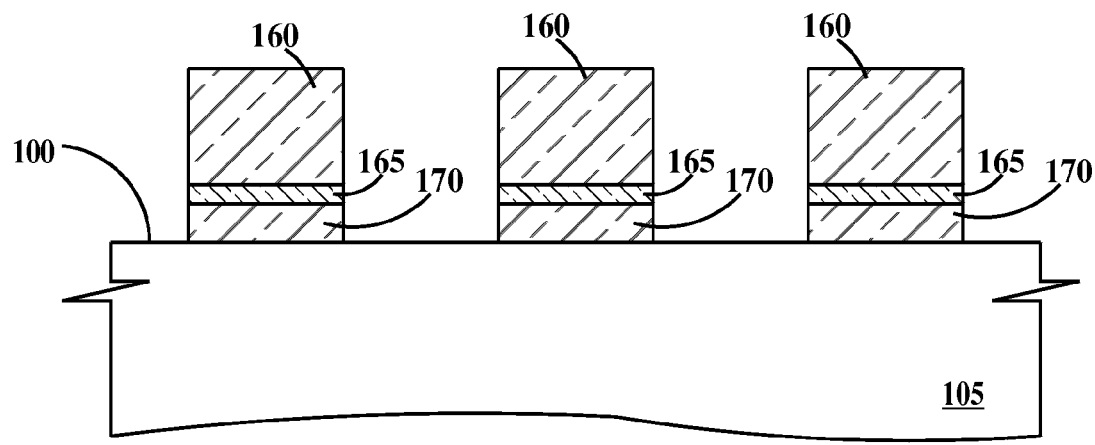

In FIG. 1E, layer 110 is etched, in one example, using a reactive ion etch (RIE) process to form islands 170 of layer 110 (see FIG. 1D) and exposing top surface 100 of substrate 105 where the substrate is not covered by the islands.

Figure 1F:
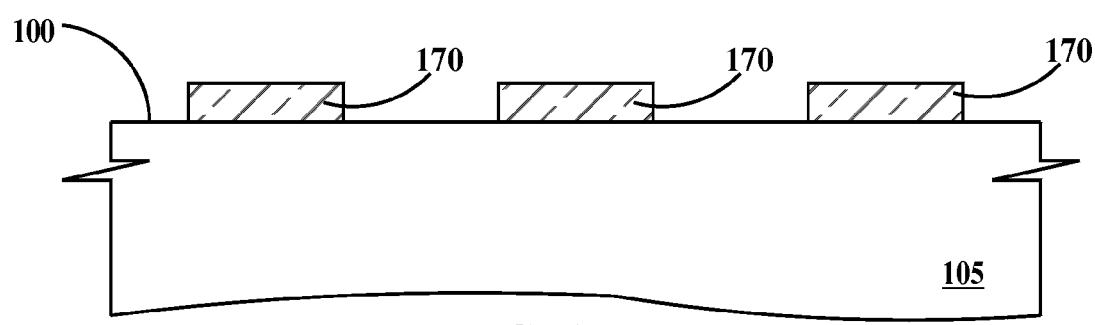

In FIG. 1F, photoresist islands 160 and ARC islands 165 are removed.

Figure 1G:
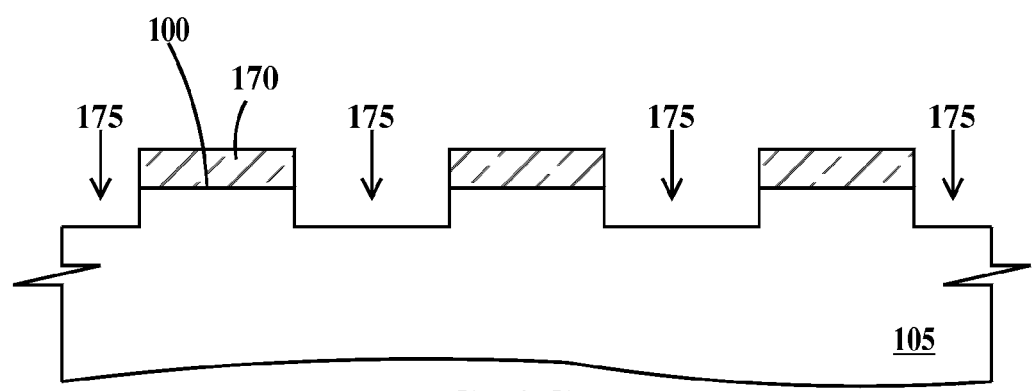

The operation illustrated in FIG. 1G is optional. In FIG. 1G, trenches 175 are formed in substrate 105, in one example, using a RIE process, islands 170 acting as a "hard" etch mask.

Alternatively, if there is no layer 110 (see FIG. 1A), trenches 175 are formed in substrate 105, in one example, using a RIE process, photoresist islands 160 (see FIG. 1D) acting as a "soft" etch mask.

General DMA Synthesis

The protected DMA glucosides (I), citrates (II), cholates (III) and adamantanedicarboxylates (IV) where the protecting group is represented by an ethoxyethyl group (V) were prepared by treatment of the glucoside, cholate, citrate or adamantanedicarboxylate with the acetal-forming reagent ethyl vinyl ether in the presence of pyridinium p-toluenesulfonate in ether or tetrahydrofuran (THF) solvent.

The protected DMA glucosides (I), citrates (II), cholates (III) and adamantanedicarboxylates (IV) where the protecting group is represented by a tetrahydrofuranyl group (VI) were prepared by treatment of the glucoside, cholate, citrate or adamantanedicarboxylate with the acetal-forming reagent dihydrofuran in the presence of pyridinium p-toluenesulfonate in ether or THF solvent.

The products were purified by silica gel column chromatography and characterized by H-NMR and TLC Preparation of Tetrahydrofuranyl
3,7,12-tris-(2-oxytetrahydrofuran)cholanoate
(Cholic-THF)

To a 250-milliliter 3-necked round-bottomed flask, equipped with a 50-milliliter pressure-equalizing addition funnel, nitrogen inlet, thermowell with digital temperature readout and a magnetic stirbar, was added 10.0 gram (0.0245 moles) of cholic acid, 2.46 gram (0.0098 moles) of pyridinium p-toluenesulfonate and 80 milliliter of anhydrous THF. The addition funnel was charged with 14.8 milliliter (0.196 moles) of 2,3-dihydrofuran and 20 milliliter of anhydrous THF. The dihydrofuran solution was added over 45 minutes with no external cooling to the cholic acid suspension. A slight exotherm was observed. The resulting suspension was stirred overnight at room temperature by which time it had become a solution. The solution was diluted with 200 milliliter of diethylether and washed, in turn, with water, saturated sodium bicarbonate solution, water and brine. The resulting organic layer was stirred with anhydrous magnesium sulfate for 1 hour, filtered, and evaporated to a yellow oil. The oil was re-dissolved in 50 milliliter of ether and passed through a short column of sequential layers of silica gel, sodium carbonate, activated charcoal and Celite. The material was eluted with 300 milliliter of ether and the eluant evaporated on a rotary evaporator to yield 14.9 grams of the title compound as a clear colorless oil. TLC (75% ether/25% pentane) showed one spot (iodine) at $R_f$ 0.65.

Preparation of 1,3-Adamantanediacetic Acid
Substituted with α-angelicalactone 1,3-Adamantanediacetic acid (5.05 gram, 0.02 mole), α-angelicalactone (7.85 gram, 0.08 mole), and 10 milliliter anhydrous THF were placed in a 100 milliliter round bottom flask equipped with a magnetic stirbar. To this mixture was added 100 milligram of p-toluenesulfonic acid monohydrate and the mixture was heated to mild reflux under nitrogen with stirring. After 17 hours, the solution was cooled to room temperature and quenched with 0.2 milliliter of concentrated ammonium hydroxide. This solution was added dropwise into a mixture of 400 milliliter of de-ionized water and 8 milliliter of concentrated ammonium hydroxide solution. The precipitated material was re-dissolved in 50 milliliter dichloromethane. This solution was washed with 50 milliliter saturated sodium bicarbonate solution followed by 50 milliliter of saturated sodium chloride solution and dried over anhydrous magnesium sulfate for 30 minutes. The solvent was removed on a rotary evaporator and the residue was dried under vacuum to give 3.50 grams of the title compound as a clear, colorless oil.

Control Positive Photoresist Formulation

A control positive CA photoresist was formulated containing 12% by weight of (3-(5-Bicyclo-[2,2,1]heptene-2-yl)-1, 1,1-trifluoro-2-(trifluoromethyl)-2-propanol) (NBHFA) homopolymer, 2% by weight Iodonium perfluorooctanesulfonate (1-PFOS) and 3% (MD-PFBUS) as the PAG, and 0.2% by weight tetrabutyl ammonium hydroxide (TBAH) in propylene glycol methyl ether acetate (PGMEA) solvent.

Experimental Positive Photoresist Formulation

An experimental positive CA photoresist was formulated containing 15% by weight of the DMA tetrahydrofuranyl 3,7,12-tris-(2-oxytetrahydrofuran)cholanoate (preparation described supra), 12% by weight of (3-(5-Bicyclo-[2,2,1] heptene-2-yl)-1,1,1-trifluoro-2-(trifluoromethyl)-2-propanol) (NBHFA) homopolymer, 2% by weight Iodonium perfluorooctanesulfonate (1-PFOS) and 3% (MD-PFBUS) as the PAG, and 0.2% by weight tetrabutyl ammonium hydroxide (TBAH) in propylene glycol methyl ether acetate (PGMEA) solvent.

Experimental Positive Photoresist Evaluation

A silicon substrate was coated with 3000 Å of the experimental positive photoresist described supra. The coating was baked at between about 90° C.-110° C. for 1 minute to drive off the solvent. The coating was then exposed at 193 nm (at doses ranging from about 15 mJ/cm$^2$ to about 100 mJ/cm$^2$) and post exposure baked at temperatures ranging from about 26° C. to about 90° C. for 1 minute. In all cases the photoresist coating was developed with 0.263 N tetramethyl ammonium hydroxide. After development, 130 nm line/130 nm space photoresist patterns showing sharp contrast were obtained.

Figure 2A:
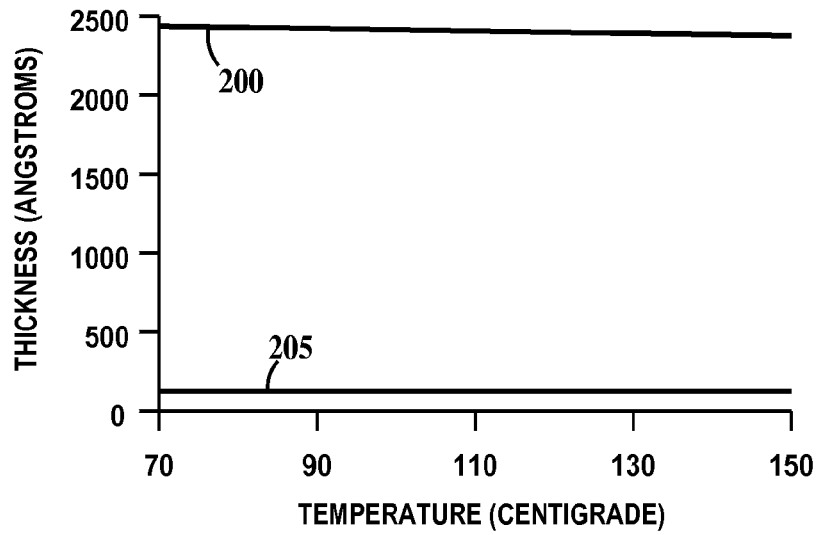
FIG. 2A is plot of photoresist thickness versus post exposure bake temperature for a control photoresist formulation.

FIG. 2A is plot of photoresist thickness versus post exposure bake temperature for a control photoresist formulation. In FIG. 2A, the control photoresist (NBHFA) described supra was coated on a substrate and baked after exposure at the temperatures indicated. Curve 200 gives the photoresist thickness as a function of temperature before development and curve 205 gives the photoresist thickness as a function of temperature after development. Curve 205 is greater than zero because the style tool used to make the measurement could not register below about 100 Å. FIG. 2A shows that the exposed polymer of the control photoresist was soluble in aqueous developer over the entire post exposure bake temperature range.

Figure 2B:
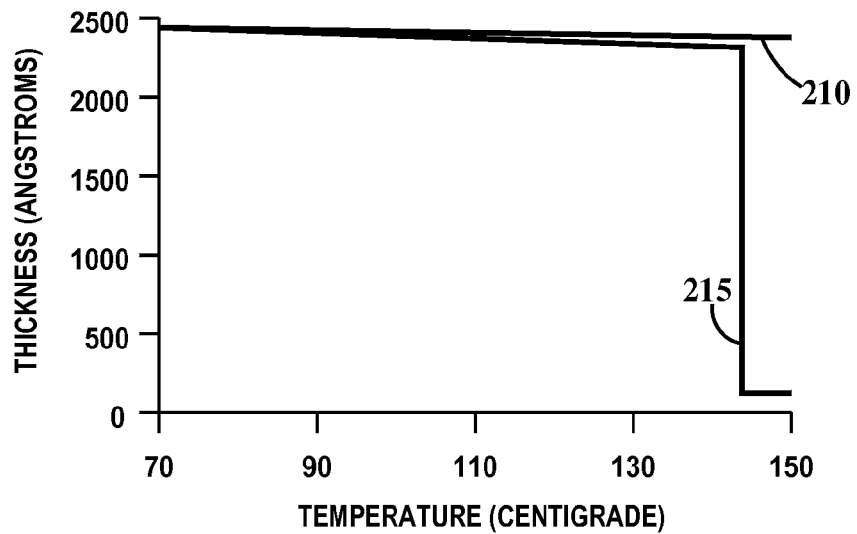
FIG. 2B is plot of photoresist thickness versus post exposure bake temperature for an experimental photoresist formulation according to an embodiment of the present invention.

FIG. 2B is plot of photoresist thickness versus post exposure bake temperature for an experimental photoresist formulation according to an embodiment of the present invention. In FIG. 2B, the experimental photoresist (NBHFA+Cholic-THF) described supra was coated on a substrate and baked after exposure at the temperatures indicated. Curve 210 gives the photoresist thickness as a function of temperature before development and curve 215 gives the photoresist thickness as a function of temperature after development. Curve 215 is greater than zero because the Alpha Step tool used to make the measurement could not register below about 100 Å. FIG. 2B indicates that the exposed polymer of the experimental photoresist was prevented from dissolving (average thinning rate over the temperature range 70° C. to 144° C. was less than about 0.6 Å/second) in aqueous developer by the added DMA until a temperature of about 144° C., which is the thermal breakdown temperature of the protecting groups of cholic-THF. The inhibition strength [dissolution rate without DMA ($DR_o$)/dissolution rate with DMA ($DR_A$)] was 63,333.

Figure 3:
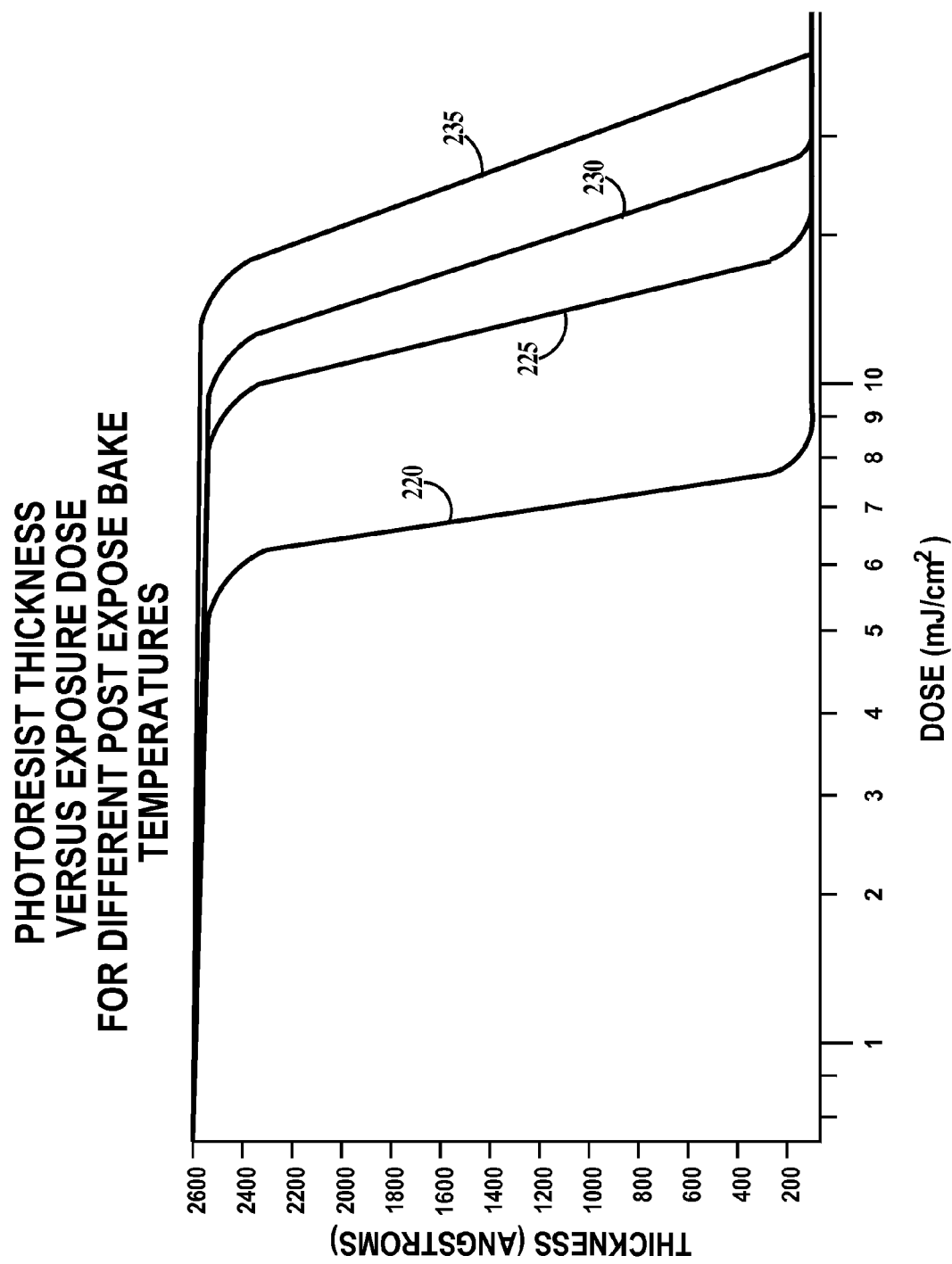
FIG. 3 is plot of photoresist thickness versus actinic radiation dose as a function of post exposure bake temperature for an experimental photoresist formulation according to an embodiment of the present invention.

FIG. 3 is plot of photoresist thickness versus actinic radiation dose as a function of post exposure bake temperature for an experimental photoresist formulation according to an embodiment of the present invention. The curves of FIG. 3 are also known as dose response curves or contrast curves. In FIG. 3, a sample of the experimental photoresist (NBHFA+Chloic-THF) described supra, was coated on a silicon substrate, pre exposure baked at 90° C., exposed at 193 nm at the doses indicated, post exposure baked at 26° C. for curve 220, 50° C. for curve 225, 65° C. for curve 230 and 105° C. for curve 235 using a thermal gradient plate (TGP) and developed in 0.263 N tetramethyl ammonium hydroxide for 60 seconds. The curves of FIG. 3 show that the photoresist compositions using DMAs of the embodiments of the present invention are relatively high contrast photoresists and operate over a wide range of post exposure bake temperatures.

Thus, the embodiments of the present invention provide new photoresist compositions having improved image resolution capability, improved methods of patterning substrates and improved DMA materials.

The description of the embodiments of the present invention is given above for the understanding of the present invention. It will be understood that the invention is not limited to the particular embodiments described herein, but is capable of various modifications, rearrangements and substitutions as will now become apparent to those skilled in the art without departing from the scope of the invention. Therefore it is intended that the following claims cover all such modifications and changes as fall within the true spirit and scope of the invention.

The invention claimed is:

1. A dissolution modification agent represented by one of the following structures:

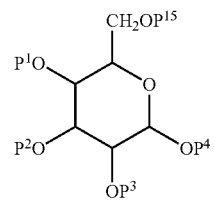

(I)

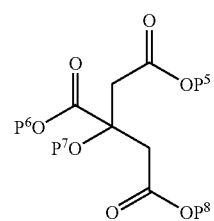

(II)

wherein each $P^1$, $P^2$, $P^3$, $P^4$, $P^5$, $P^6$, $P^7$, $P^8$, and $P^{15}$ is independently selected from the group consisting of a structure V, a structure VI and a structure VII:

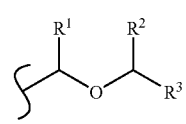

(V)

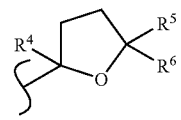

(VI)

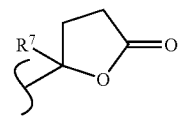

(VII)

wherein each $R^1$, $R^2$, $R^3$, $R^4$, $R^5$, $R^6$ and $R^7$ is independently selected from the group consisting of a hydrogen atom, a hydrocarbyl group having 4 to 12 carbon atoms, a substituted hydrocarbyl group having 4 to 12 carbon atoms, a heterohydrocarbyl group having 4 to 12 carbon atoms, and a substituted heterohydrocarbyl group having 4 to 12 carbon atoms; and wherein any two $R^1$, $R^2$, $R^3$ or any two $R^4$, $R^5$, $R^6$ may be linked to form a three to eight-membered cyclic group.

2. The dissolution modification agent of claim 1, wherein said dissolution modification agent has the property of being insoluble in aqueous alkaline developer.

3. The dissolution modification agent of claim 1, wherein said dissolution modification agent has the property of being soluble in aqueous alkaline developer after exposure to ultraviolet radiation.

4. The dissolution modification agent of claim 1, wherein said dissolution modification agent has the property of being soluble in aqueous alkaline developer after exposure to ultraviolet radiation having a wavelength of about 250 nm or less.

5. The dissolution modification agent of claim 1, wherein said dissolution modification agent has the property of being hydrophobic.

6. The dissolution modification agent of claim 1, wherein said dissolution modification agent has the property of being hydrophobic and becoming hydrophilic after heating to a temperature above 26° C. but no greater than about 100° C.

7. The dissolution modification agent of claim 1, wherein said dissolution modification agent is soluble in a solvent selected from the group consisting of cyclohexanone, ethyl lactate, propylene glycol methyl ether acetate, gamma-butyrolactone and combinations thereof.

8. The dissolution modification agent of claim 1, comprising:
the structure (I).

9. The dissolution modification agent of claim 1, comprising:
the structure (I); and
wherein each $P^1$, $P^2$, $P^3$ and $P^{15}$ is structure (V).

10. The dissolution modification agent of claim 1, comprising:
the structure (I); and
wherein each $P^1$, $P^2$, $P^3$ and $P^{15}$ is structure (VI).

11. The dissolution modification agent of claim 1, comprising:
the structure (I); and
wherein each $P^1$, $P^2$, $P^3$ and $P^{15}$ is structure (VII).

12. The dissolution modification agent of claim 1, wherein:
structure (I) is a glucoside; and
wherein each $P^1$, $P^2$, $P^3$ and $P^{15}$ is a same ethoxyethyl group.

13. The dissolution modification agent of claim 1, wherein:
structure (I) is a glucoside; and
wherein each $P^1$, $P^2$, $P^3$ and $P^{15}$ is a same thetrahydrofuranyl group.

14. The dissolution modification agent of claim 1, comprising:
the structure (II).

15. The dissolution modification agent of claim 1, comprising:
the structure (II); and
wherein each $P^5$, $P^6$, $P^7$ and $P^8$ is structure (V).

16. The dissolution modification agent of claim 1, comprising:
the structure (II); and
wherein each $P^5$, $P^6$, $P^7$ and $P^8$ is structure (VI).

17. The dissolution modification agent of claim 1, comprising:
the structure (II); and
wherein each $P^5$, $P^6$, $P^7$ and $P^8$ is structure (VII).

18. The dissolution modification agent of claim 1, wherein:
structure (II) is a citrate; and
wherein each $P^1$, $P^2$, $P^3$ and $P^{15}$ is a same ethoxyethyl group.

19. The dissolution modification agent of claim 1, wherein:
structure (II) is a citrate; and
wherein each $P^1$, $P^2$, $P^3$ and $P^{15}$ is a same thetrahydrofuranyl group.

20. The dissolution modification agent of claim 1, wherein:
structure (I) is a glucoside; and
wherein each $P^1$, $P^2$, $P^3$ and $P^{15}$ is a same angelicalactone group.

* * * * *